US008886268B2

(12) United States Patent
Kanayama

(10) Patent No.: US 8,886,268 B2
(45) Date of Patent: Nov. 11, 2014

(54) LIVING BODY INFORMATION MEASURING APPARATUS

(71) Applicant: Shoichi Kanayama, Otawara (JP)

(72) Inventor: Shoichi Kanayama, Otawara (JP)

(73) Assignees: Kabushiki Kaisha Toshiba, Tokyo (JP); Toshiba Medical Systems Corporation, Tokyo (JP)

( * ) Notice: Subject to any disclaimer, the term of this patent is extended or adjusted under 35 U.S.C. 154(b) by 10 days.

(21) Appl. No.: 13/648,822

(22) Filed: Oct. 10, 2012

(65) Prior Publication Data

US 2013/0041237 A1     Feb. 14, 2013

Related U.S. Application Data

(60) Division of application No. 12/028,410, filed on Feb. 8, 2008, now Pat. No. 8,600,466, which is a continuation of application No. 11/287,250, filed on Nov. 28, 2005, now Pat. No. 7,389,131, which is a continuation of application No. PCT/JP2004/010261, filed on Jul. 13, 2004.

(30) Foreign Application Priority Data

Jul. 22, 2003   (JP) ................. 2003-199827

(51) Int. Cl.
*A61B 5/1455*     (2006.01)
*A61B 5/145*      (2006.01)

(52) U.S. Cl.
CPC ........... *A61B 5/1455* (2013.01); *A61B 5/14532* (2013.01)
USPC ........................................ 600/310

(58) Field of Classification Search
USPC ......... 600/309, 310, 316, 318, 319, 320, 322, 600/323
See application file for complete search history.

(56) References Cited

U.S. PATENT DOCUMENTS

| 4,407,290 A | * | 10/1983 | Wilber ......................... 600/330 |
| 5,246,002 A |   | 9/1993  | Prosser |
| 5,735,799 A |   | 4/1998  | Baba et al. |
| 5,974,338 A |   | 10/1999 | Asano et al. |
| 6,088,605 A | * | 7/2000  | Griffith et al. ............... 600/316 |
| 6,332,683 B1 |  | 12/2001 | Ono et al. |
| 6,801,799 B2 | * | 10/2004 | Mendelson .................. 600/330 |
| 7,519,406 B2 | * | 4/2009  | Blank et al. .................. 600/310 |

(Continued)

FOREIGN PATENT DOCUMENTS

| EP | 0 290 272 A1 | 11/1988 |
| EP | 0 897 691 A2 A3 | 2/1999 |

(Continued)

OTHER PUBLICATIONS

English Translation of JP 11123195 to JIYO.

(Continued)

*Primary Examiner* — Eric Winakur
(74) *Attorney, Agent, or Firm* — Oblon, Spivak, McClelland, Maier & Neustadt, L.L.P.

(57) ABSTRACT

A living body information measuring apparatus includes an optical system for irradiating light to a subject and detecting light from the subject, a signal processing portion for acquiring information with regard to a tissue condition of the subject based on a detecting signal of light, and a position determining portion for determining an acceptability of an irradiating position of light based on the detecting signal of light.

6 Claims, 7 Drawing Sheets

(56) References Cited

U.S. PATENT DOCUMENTS

| | | |
|---|---|---|
| 2002/0038080 A1 | 3/2002 | Makarewicz et al. |
| 2003/0060692 A1 | 3/2003 | Ruchti et al. |
| 2003/0139687 A1 | 7/2003 | Abreu |
| 2005/0004458 A1 | 1/2005 | Kanayama et al. |
| 2005/0187871 A1 | 8/2005 | Kanayama et al. |

FOREIGN PATENT DOCUMENTS

| | | |
|---|---|---|
| JP | 1-214336 | 8/1989 |
| JP | 6-217952 | 8/1994 |
| JP | 8-196526 | 8/1996 |
| JP | 2628689 | 4/1997 |
| JP | 2001-153796 | 6/2001 |
| JP | 2001-190500 | 7/2001 |
| JP | 3303299 | 5/2002 |
| JP | 2002-336210 | 11/2002 |
| WO | WO 94/15525 | 7/1994 |
| WO | WO 99/01745 | 1/1999 |
| WO | WO 02/10748 A2 | 2/2002 |
| WO | WO 2004/042382 A1 | 5/2004 |

OTHER PUBLICATIONS

Extended European Search Report issued Jul. 27, 2011 in Patent Application No. 111072441.5.

* cited by examiner

LIVING BODY INFORMATION MEASURING APPARATUS

CROSS REFERENCE TO RELATED APPLICATIONS

This application is a divisional application of U.S. application Ser. No. 12/028,410, filed Feb. 8, 2008, which is a continuation application of U.S. patent application Ser. No. 11/287,250, filed on Nov. 28, 2005, now U.S. Pat. No. 7,389,131, which is a continuation of PCT Application No. PCT/JP2004/010261, filed Jul. 13, 2004, which was published under PCT Article 21(2) in Japanese, which is based upon and claims the benefit of priority from prior Japanese Patent Application No. 2003-199827, filed Jul. 22, 2003. The entire contents of each of the above applications are incorporated herein by reference.

BACKGROUND OF THE INVENTION

1. Field of the Invention

The present invention relates to a living body information measuring apparatus for optically measuring non-invasively a concentration of a substance in the blood or in the body fluid in the biological tissue cell or outside the biological tissue cell, or opt-physical information of the biological tissue for health care, diagnosis or treatment of diseases, or beauty care, particularly relates to a biological information measuring apparatus for non-invasively measuring information with regard to blood composition concentration of glucose, cholesterol, neutral fat, proteins such as albumin, hemoglobin, and creatine or the like, body gas concentration of oxygen or carbon dioxide, concentration of alcohol, a drug or the like, or information with regard to denaturing the biological tissue represented by cancer, inflammation, skin moisture holding function, arteriosclerosis or the like by using visible light, near infrared light, or middle infrared light or the like.

2. Description of the Related Art

As a representative background art apparatus for measuring a composition or a concentration of a substance present in a subject, there is a blood glucose meter for measuring a glucose concentration (blood glucose value) in the blood or in the body fluid. Currently, a widely used blood glucose meter utilizes a small amount of blood sample sampled by piercing a needle to a portion of the finger, the arm or the like of the subject and a concentration thereof is measured by chemically reacting glucose in the sampled blood.

Further, as the most general method of measuring the glucose concentration, there is a method of using an enzyme electrode. As an enzyme used in detecting glucose, there is, for example, glucose oxidase (GOD). By fixing the enzyme to a polymer film or the like and bringing glucose in the substance of the subject into contact with the GOD fixed film, oxygen is consumed, and the glucose concentration can be measured by detecting a change in the enzyme. The blood glucose meter of the blood sampling type is constituted by a portable size and is utilized for monitoring the blood glucose level of a diabetic patient.

However, according to the above-described method, it is necessary to pierce a needle to a portion of the finger, the arm or the like for sampling the blood, the skin of the subject is damaged and the subject is accompanied by pain. Therefore, although it is preferable to carry out measurement by 5 times or more per day for strictly controlling the blood glucose level of the diabetic patient, in a current state, a number of times of measurement stay to be typically 2 or 3 times per day.

There is investigated a method of sampling and measuring a small amount of the interstitial fluid by opening a small hole to a degree of not being accompanied by pain on a surface of the skin by using a small needle or laser, or a method of sampling and measuring an effluent solution of the interstitial fluid or the like by improving effluent permeability of the skin by applying voltage or ultrasonic wave to the surface of the skin with an object of alleviating the damage of the skin or the pain of the patient.

On the other hand, as a method of non-invasively measuring a component or a concentration of a substance present in the subject of glucose or the like without necessitating to sample the blood or sample the interstitial fluid, a method of utilizing an electromagnetic wave is known (for example, JP-B-5-58735 (pages 3-5, FIGS. 1-5)).

The method is a method of measuring a composition or a concentration of a substance present in the subject by irradiating the surface of the skin of the subject or the like with a plurality of different wavelengths of near infrared light, classifying detecting signals thereof into a reference signal and a measuring signal and operating to process values thereof. Here, an electromagnetic wave having a wavelength band of about 380 through 770 nm is defined as visible light, an electromagnetic wave having a wavelength band of about 770 through 2500 nm is defined as near infrared light, an electromagnetic wave having a wavelength band of about 2500 through 25000 nm is defined as middle infrared light and an electromagnetic wave having a wavelength band of about 25 through 100 µm is defined as far infrared light.

In the above-described method, as a light source of near infrared light, there is used a method of spectroscopically dividing light emitted from a white light source of tungsten-halogen lamp or the like into a prescribed wavelength by spectroscopic means of an interference filter or the like, monochromatic light or a semiconductor laser (LD) or a light emitting diode (LED) for emitting light near to monochromatic light. Further, as a detector of near infrared light transmitted and diffused in the subject, an optical detector such as photodiode (PD) is used.

The above-described non-invasive spectroscopic analysis of the biological substance using near infrared light, or further, visible light is a method attracting attention in recent years, and is provided with an advantage that an aqueous solution system can be analyzed and a function of permeating the organism is high since absorption of water occupying a large portion as a constituent element of the organism is small in comparison with the spectroscopic analysis using middle or far infrared light. On the other hand, the analysis has a disadvantage that a signal ascribed to molecular vibration is about one hundredth as small as a middle infrared light region and ascription of the signal is difficult to be specified.

Further, also in measurement using near infrared light, according to near infrared light in a region near first harmonic of water (1250 through 1800 nm), a spectral signal ascribed to molecular vibration is comparatively large, on the other hand, transmittivity of light is poor, and near infrared light in a region near second harmonic of water (800 through 1300 nm) is provided with a characteristic that a spectral signal ascribed to molecular vibration is small, on the other hand, transmittivity of light is excellent.

That is, when a signal of a biologic substance constituting an object thereof is detected in a near infrared region, a problem occurs in that there are a number of cases in which a signal in correspondence with a change in a concentration of the biological substance constituting the object is very small and ascription of the signal is not clear. As a method of resolving such a problem, there is a statistically analyzing method, or multivariate analyzing method (refer to, for example, JP-A-10-325794 (pages 4-9, FIGS. 1-8)).

Although the analyzing methods are excellent methods in detecting a small change in a signal and accurately quantifying a substance, the methods do not improve a signal to noise ratio (SN ratio) of a signal constituting an index of biological substance information constituting the object.

As a method of improving the SN ratio, there is used a method of making a change (variation) in a concentration of a biological substance constituting the object clear by calculating a difference between a reference signal and a signal related to substance information constituting the object, or a ratio thereof, or a method of reducing a noise component by averaging signals measured by a plurality of times.

Further, when light transmitted and diffused in the subject tissue by irradiating light to the subject is detected, there is a case in which noise is increased by superposing and measuring light which is not related to information constituting an index of a condition of the tissue scattered or reflected at a surface of the tissue of the subject or input and output portions of light of a measuring instrument other than an optical signal having information constituting the index of the condition of the tissue of the subject.

As a measuring method for resolving such a problem, there is a local diffuse reflectance method for calculating a light absorbing degree of a substance from a plurality of measured data substantially having different diffusion light optical path lengths by changing a distance between an irradiating point and a light receiving point (refer to, for example, International Publication WO99/59464 (page 7, FIG. 1)).

According to the method, a plurality of optical fibers are brought into direct contact with a surface of a measuring portion of a subject, light is detected at a plurality of portions in which irradiating positions and light detecting positions spatially differ from each other and therefore, detection of a noise signal generated by scattering or reflecting light at the surface of the tissue of the subject or at input and output sites of light of the measuring instrument can be restrained.

Further, there is also disclosed a method of constituting a plurality of light sources and detectors in a shape of an array and irradiating and receiving light by way of an optical fiber plate (refer to, for example, specification of U.S. Pat. No. 5,893,364 (pages 7-8, FIGS. 1-2)).

An optical characteristic of the tissue of the organism differs by an individual difference or a region. The difference in the optical characteristic effects a significant influence on measuring accuracy. For example, when there is the blood vessel or the like in an optical path, an optical signal is varied by an influence of beat of the blood. As a method constituting an object by achieving promotion of measuring accuracy by restraining the optical characteristic influence which differs by the individual difference or the region, there is a method of accurately sampling desired information reflected with a condition of the tissue of the subject by irradiating a plurality of wavelengths of light, collecting an optical signal diffused, transmitted or reflected in the subject at that occasion and carrying out processing of cross correlation or the like from the information (refer to, for example, JP-A-10-325794 (pages 4-9, FIGS. 1-8)).

Further, as a method of restraining influence of a difference of an optical characteristic by a difference by positions, there is disclosed a method of taking an image of a portion of a subject including a portion to be irradiated with light to constitute image information by using an image taking element of a charge coupled device or the like and controlling a position of irradiating light to be the same at each time of measurement from the image information (refer to, for example, JP-A-11-128176 (pages 2-4, FIGS. 1-2)).

Further, it has been clarified that a measurement result is varied depending on a temperature of a portion to be measured and as a method of resolving the problem, there is disclosed a method of controlling a temperature of the measured site, a method of measuring and correcting a temperature of the measured site (refer to, for example, JP-A-11-123195 (pages 3-4, FIGS. 4-8)).

Further, in order to efficiently make light invade inside of the subject and promote a function of detecting light reaching outside of the subject by being diffused, transmitted or reflected in the subject, there is also a method of improving a performance of bringing a subject and a measuring apparatus into contact with each other by using a manchette (compressing band) utilized in a blood pressure meter or the like at input and output portions of light and vicinities thereof.

With regard to a non-invasive measurement of a composition or a concentration of a substance present in the subject other than a glucose concentration (blood glucose value), for example, an apparatus of measuring a hemoglobin concentration in the capillary, an apparatus for measuring an oxygen saturation degree or the like has been put into practice. Further, it is desired to develop an apparatus of non-invasively and quantitatively measuring various kinds of biological information starting from cholesterol to neutral fat which are important organism substances related to life-style related diseases similar to glucose.

In an apparatus optically measuring and analyzing noninvadingly information with regard to a composition or a concentration of a substance present in a subject, or denaturing the subject tissue, a problem arises in that a measured position or a measuring condition of a subject is varied at each measurement, a measurement result differs depending on a position of a measured portion owing to a difference of the tissue of the subject or the like.

BRIEF SUMMARY OF THE INVENTION

It is an object of the invention to provide a living body information measuring apparatus capable of accurately carrying out a quantitative analysis or a qualitative analysis of a tissue condition of a subject by swiftly and accurately measuring optical information related to a composition, a concentration of the body fluid or the tissue of the subject, or a change in a physical property thereof by preventing a failure of measurement owing to the fact that a measured portion or a measuring condition is improper.

A living body information measuring apparatus of the invention is a biological information measuring apparatus capable of non-invasively acquiring information with regard to a tissue condition of a subject by irradiating light to the subject and detecting light diffused, transmitted or reflected in the subject, characterized in including position determining means for determining an acceptability of a measured site or measurement at a position of the measured site based on a detecting signal of the light.

According to the invention, by controlling a measured site such that the measured position is disposed at an optimum location and optimizing a measuring condition, promotion of a measurement accuracy of a quantitative analysis or a qualitative analysis of a tissue condition of the organism can be achieved by preventing a failure of measurement owing to the fact that the measured location is improper.

DETAILED DESCRIPTION OF THE INVENTION

First Embodiment

An explanation will be given of a first embodiment of a living body information measuring apparatus according to the invention in reference to the drawings as follows.

Figure 1:
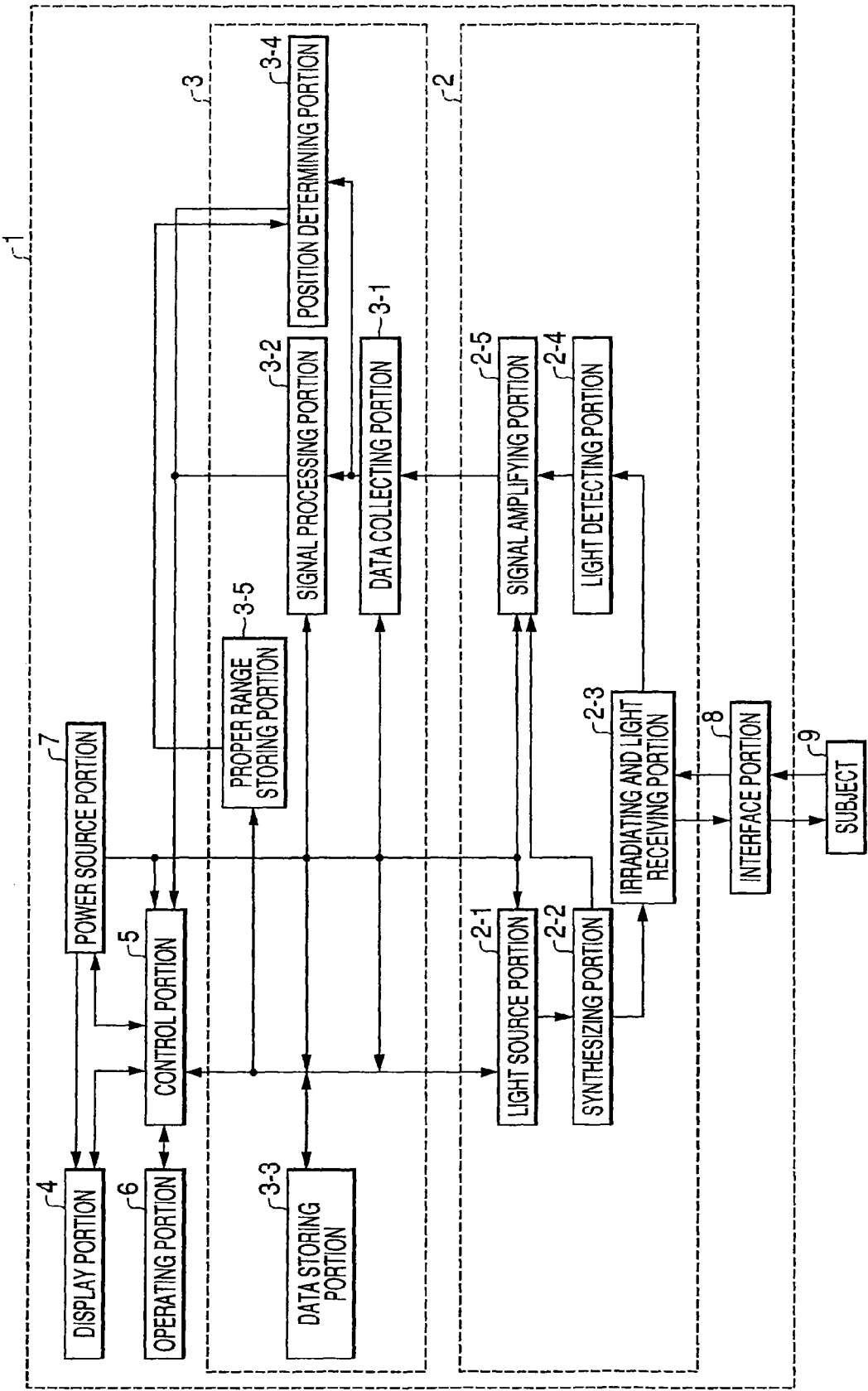
FIG. 1 is a block diagram showing a constitution of a first embodiment of a living body information measuring apparatus according to the invention.

FIG. 1 is a block diagram showing a constitution of a first embodiment of a living body information measuring apparatus according to the invention.

A first embodiment uses a space disintegrated diffusion and reflection method for calculating a light absorbing degree of a substance from a plurality of measured data substantially having different diffusion light optical path lengths by changing a distance between an irradiating point and a light receiving point described in Patent Reference 3, and a method of utilizing a plurality of wavelengths of light described in Patent Reference 2.

The living body information measuring apparatus 1 is provided with an interface portion 8, an optical system 2, a data processing system 3, a display portion 4, a control portion 5, an operating portion 6 and a power source portion 7.

The optical system 2 includes a light source portion 2-1. The light source portion 2-1 generates one or a plurality of monochromatic light, or light near thereto. A wave synthesizing portion 2-2 superposes light from the light source portion 2-1 on the same optical axis. An irradiating and light receiving portion 2-3 controls the optical axis of light. Light from the irradiating and light receiving portion 2-3 is irradiated to a measured portion of a subject 9 via the interface portion 8.

Light diffused, transmitted or reflected in the subject 9 is received by the irradiating and light receiving portion 2-3, received light is detected by a light detecting portion 2-4 to convert it into an electric signal, and the electric signal is amplified by a signal amplifying portion 2-5.

At this occasion, an intensity of an optical signal detected from the signal amplifying portion 2-5 at a portion diffused, transmitted or reflected in the subject 9 depends on a rate of presence of a predetermined substance present in the subject 9 or a concentration thereof.

In the light source portion 2-1, a light source for generating monochromatic light used or light near thereto is preferably a small-sized light emitting element of a semiconductor laser (LD), a light emitting diode (LED) or the like, and one or a plurality of the elements emitting light by wavelengths thereof can be used.

The data processing system 3 converts the electric signal amplified by the signal amplifying portion 2-5 of the optical system 2 into a digital signal to collect at a date collecting portion 3-1, the electric signal being subjected to signal processing by a signal processing portion 3-2, calculates information with regard to a composition or a concentration of a substance present in the subject 9, or denaturing of a subject tissue, and preserves a result thereof at a data storing portion 3-3.

Further, according to the information with regard to the composition or concentration of the subject present in the subject 9, or denaturing of the tissue of the subject 9, previously, in the subject or a desired group of subjects, from measured data provided by a biologic information measuring apparatus of the invention or a standard method, by using a statistical analyzing method or the like, a relationship between both of measured data is formed into a mathematical model, and the information is calculated in accordance with the mathematical model.

The display portion 4 includes a display lamp in which a lighted color is changed to red/green, CRT or a display of a panel type, and displays information processed by the signal processing portion 3-2, a position determining portion 3-4 of the data processing system 3 as necessary. The display portion 4 indicates a result of determining a position by the position determining portion 3-4, that is, acceptability of a determined irradiating position by the lighted color of the display light or a message display of the display under control of the control portion 5. At the display of the display portion 4, there is displayed the information with regard to the composition or the concentration of the subject present in the subject 9, or denaturing of the subject tissue processed by the signal processing portion 3-2.

The acceptability of the determined irradiating position is not limited to be indicated by light color of the display lamp or the message display of the display, for example, the acceptability may be indicated by voice or vibration in accordance with the acceptability. Vibration is generated by a vibrator driving circuit installed in the vicinity of an irradiated portion or a measured portion.

The position determining portion 3-4 determines the acceptability of the light irradiating position based on a light detecting signal of a preparatory measuring period. Specifically, the position determining portion 3-4 determines that the irradiating position is proper when intensities of a plurality of light detecting signals measured in the preparatory measuring period are converged in a proper range. Further, the position determining portion 3-4 determines that the irradiating position is proper when a width of variation of the detected signal of light is lower than a threshold. Preferably, the proper range or the threshold is classified to be used in accordance with optical characteristics with regard to invasion/scattering/reflection of light of a measured portion, skin constitution (degree of dryness of skin) of the subject, color of the skin, age or the like of the subject. A plurality of proper ranges (or thresholds) are related to a plurality of optical characteristics and stored to a proper range storing portion 3-5. The control portion 5 reads the proper range (or threshold) in correspondence with the inputted optical characteristic from the proper range storing portion 3-5 by way of the operating portion 6 to set it to the position determining portion 3-4.

Operation of the living body information measuring apparatus 1 is carried out by the operating portion 6. As a method of operation, there can be used operating means suitable for a user of the living body information measuring apparatus 1 such as a keyboard, a mouse, a button, a touch key panel, voice or the like.

The control portion 5 controls operation of the living body information measuring apparatus 1 such as the light source portion 2-1, the signal amplifying portion 2-5, the data collecting portion 3-1, the signal processing portion 3-2, the data storing portion 3-3, the proper range storing portion 3-5, the position determining portion 3-4, the display portion 4, the power source portion 7 and the like based on a signal or the like of the operating portion 6 operated by a user of the biologic information measuring apparatus 1.

The power source portion 7 supplies power to the signal amplifying portion 2-5, the display portion 4, the control portion 5, further, the control portion 5 supplies power to the data storing portion 3-3, the signal processing portion 3-2, the data collecting portion 3-1, the proper range storing portion 3-5, the position determining portion 3-4 as necessary.

Figure 2:
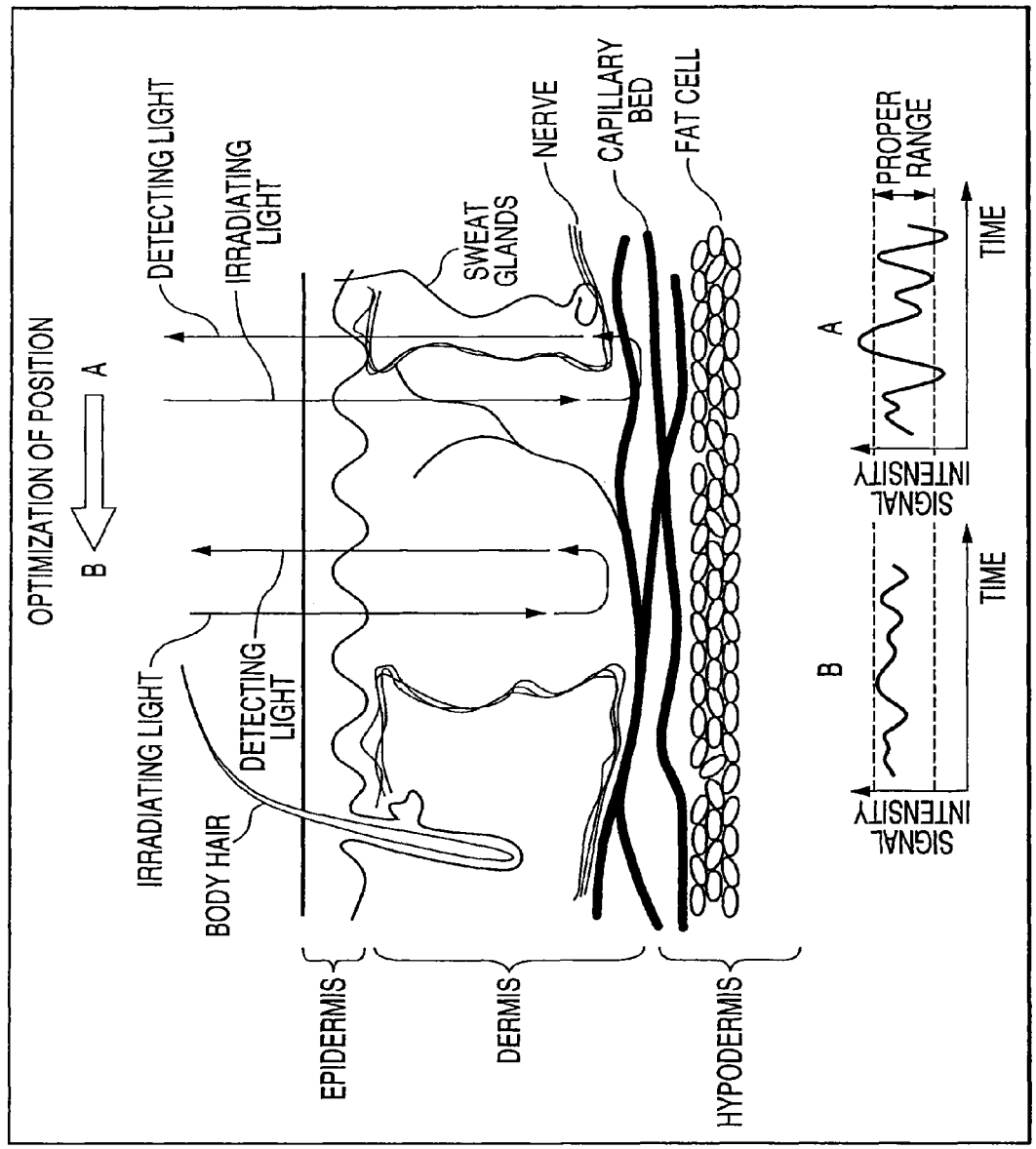
FIG. 2 is a schematic view of a preparatory measurement and position determination according to the first embodiment of the invention.

FIG. 2 schematically shows an example of a mechanism of a change in a signal by a measured portion according to the embodiment. As shown by FIG. 2, a structure of the skin of the human body is constituted by the cutis, the corium, the hypoderm in this order from the body surface. In the living body information measuring apparatus 1 according to the invention, irradiated light invades mainly from the cutis to a portion of the corium, and a portion of light reflected or scattered in the procedure is emitted to the body surface to be detected.

As shown by FIG. 2, the corium is provided with the tissue of the blood vessel, the nerve, the sweat gland, the pelage or the like, to show a complicated structure. For example, when irradiating light of the living body information measuring apparatus 1 is irradiated to the pelage portion and when the irradiated light is irradiated to other portion, signal intensities detected from a difference in the optical characteristics of the tissues significantly differ from each other. In this case, it is preferable to irradiate irradiating light to a portion other than the pelage portion.

At position A of FIG. 2, light transmits through portions of the blood vessel and the nerve and therefore, a signal is varied by an influence of, for example, beat of the blood flowing in the blood vessel. A preparatory measurement is carried out before the actual measurement. The preparatory measurement is repeated until an instruction of stopping the preparatory measurement is inputted by constituting one unit by a predetermined period of 0.5 second or the like. In the predetermined period, irradiation of light for the preparatory measurement and detection of reflected light thereof or the like are repeated. In the predetermined period, one set of light detecting signals are acquired. When a signal intensity of at least one of one set of the light detecting signals is deviated from a proper range, it is determined that the position is improper. At this occasion, the display light of the display portion 4 is lighted in red color.

On the other hand, at position B, all of one set of light detecting signals are converged into a proper range. It is determined that the position is proper. At this occasion, the display light of the display portion 4 is lighted in green color. An operator can search a position at which the display light of the display portion 4 is changed from red color to green color while moving the interface portion 8 or the like. For example, in this case, measurement is carried out by light of a wavelength which is changed depending on a concentration of hemoglobin, for example, a wavelength between 500 nm and 1600 nm and an optimum measuring position is determined from the result. Further, desired measurement of glucose or the like can be carried out at the optimum measuring position.

Figure 3:
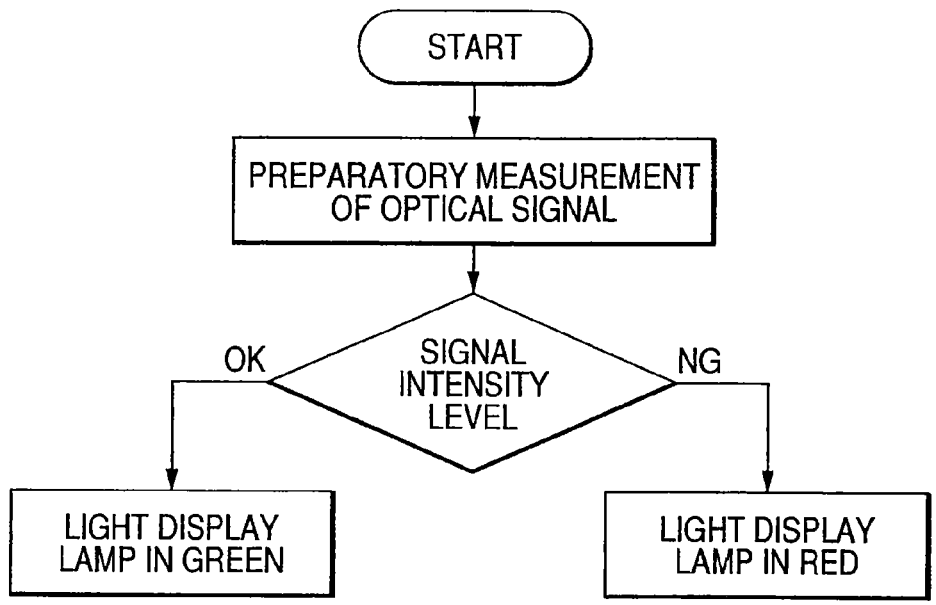
FIG. 3 is a diagram showing a procedure of a preparatory measurement processing according to the first embodiment of the invention.
Figure 4:
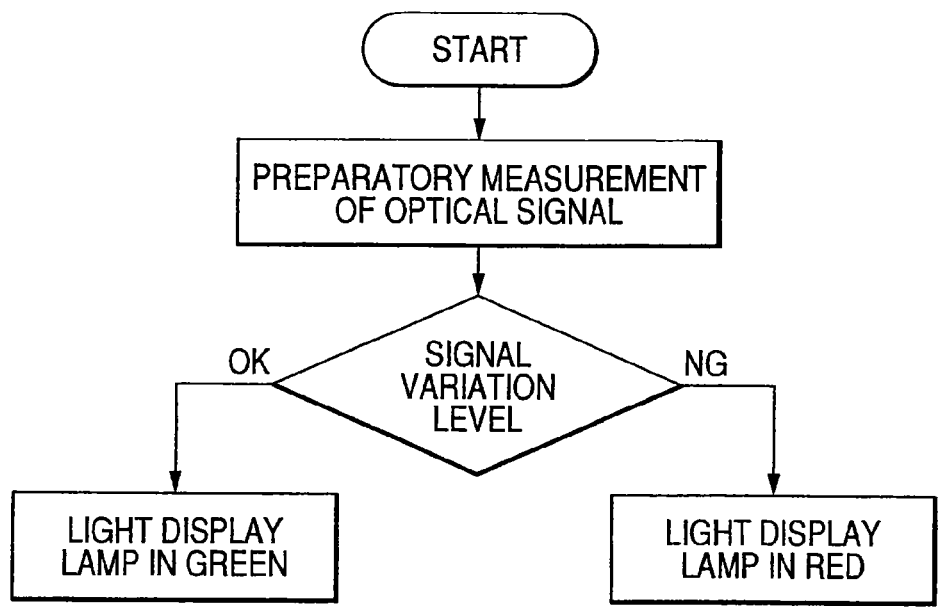
FIG. 4 is a diagram showing a procedure of a preparatory measurement processing according to the first embodiment of the invention.

FIG. 3 and FIG. 4 show a procedure of processing including a preparatory measurement of carrying out measurement of an optical signal (hereinafter, referred to as preparatory measurement), determining whether a measured portion is suitable for measurement based on the signal and finally displaying a result of the determination.

FIG. 3 shows a procedure when preparatory measurement is carried out. Preparatory measurement of 0.5 second or the like is repeated. In each preparatory measurement period, light irradiation and light reception are repeated by a predetermined number of times. Thereby, one set of light detecting signals are acquired. When all of intensities of one set of light detecting signals are converged in a proper range, it is determined that a light irradiating position (or measuring position) is proper. At that occasion, the control portion 5 controls the display portion 4 to light the display light of the detecting portion 4 in green color.

On the other hand, when an intensity of at least one light detecting signal of one set of the light detecting signals is deviated from the proper range, it is determined that a light irradiating position (or measuring position) is not proper. At that occasion, the control portion 5 controls the display portion 4 to light the display light of the display portion 4 in red color. Here, in the preparatory measurement, measurement may be carried out under the same condition as that of the actual measurement or a wavelength or an irradiating intensity may be changed from those of the actual measurement.

A point of FIG. 4 which differs from FIG. 3 resides in determining acceptability of a position from a signal variation of preparatory measurement in place of the signal intensity of FIG. 3. According to the embodiment, when a variation of one set of light detecting signals acquired in the preparatory measurement period, for example, a difference between a maximum value and a minimum value of a plurality of light detecting signals is lower than a threshold, it is determined that the light irradiating position (or measuring position) is proper (refer to FIG. 6). At that occasion, the control portion 5 controls the display portion 4 to light the display light of the display portion 4 in green color. On the other hand, when the variation of one set of the light detecting signals acquired in the preparatory measurement period, for example, the difference between the maximum value and the minimum value of the plurality of light detecting signals is the same as or exceeds the threshold, it is determined that the light irradiating position (or measuring position) is not proper. At that occasion, the control portion 5 controls the display portion 4 to light the display lamp of the display portion 4 in red color.

It is also possible to determine whether the measured portion is acceptable or not by using both of the signal intensity level and the signal variation level shown in FIG. 3 and FIG. 4.

Second Embodiment

Figure 5:
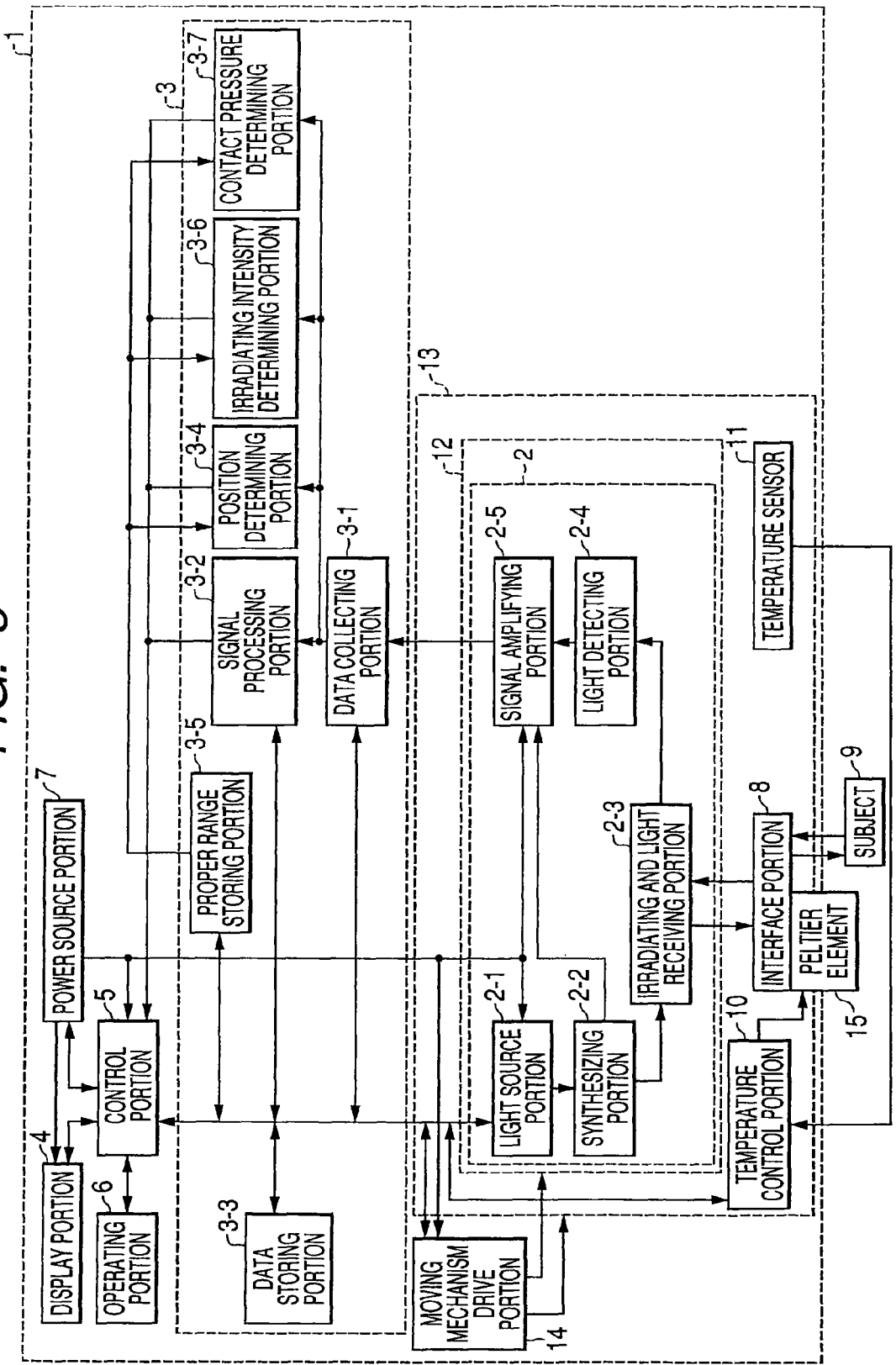
FIG. 5 is a block diagram showing a constitution of a second embodiment of a living body information measuring apparatus according to the invention.

FIG. 5 is block diagram showing a constitution of a second embodiment of a living body information measuring apparatus according to the invention. A moving mechanism drive portion 14 is added to arrange with an optical system horizontally movable portion 12 capable of moving the optical system 2, the optical system horizontally movable portion 12 is added to arrange with an optical system up and down movable portion 13 capable of moving the optical system horizontal movable portion 12 including the interface portion 8, and the interface portion 8 is added to arrange with a temperature control portion 10 for controlling a temperature of a measured portion of the subject 9 and a temperature sensor 11 for measuring the temperature of the measured portion.

The moving mechanism drive portion 14 is constituted by, for example, a drive motor and a plurality of gears, and can movably control the optical system horizontal movable portion 12 and the optical system up and down movable portion 13 by controlling a current applied from the power source portion 7 to the drive motor by the control portion 5.

The data processing system 3 is provided with an irradiation intensity determining portion 3-6, a contact pressure determining portion 3-7 along with the position determining portion 3-4.

The temperature sensor 11 is embedded in the interface portion 8 with the organism for measuring a temperature of the body surface of the subject. The temperature sensor 11 is constituted by a thermoelectric body, a thermistor or the like. The temperature control portion 10 supplies a current to a Peltier element 15 constituting a heat source attached to a bottom face portion of the interface portion 8 in accordance with a temperature detected by the temperature sensor 11 such that the temperature detected by the temperature sensor 11 becomes a temperature suitable for starting the actual measurement. The interface portion 8 is constituted by, for example, a metal material of aluminum or the like having an excellent heat conductivity as a heat interface member with the organism such that heat generated by the Peltier element 15 is transferred to a total face of the interface portion 8.

A procedure of a measurement processing using the constitution of the second embodiment according to the invention will be shown as follows.

Figure 6:
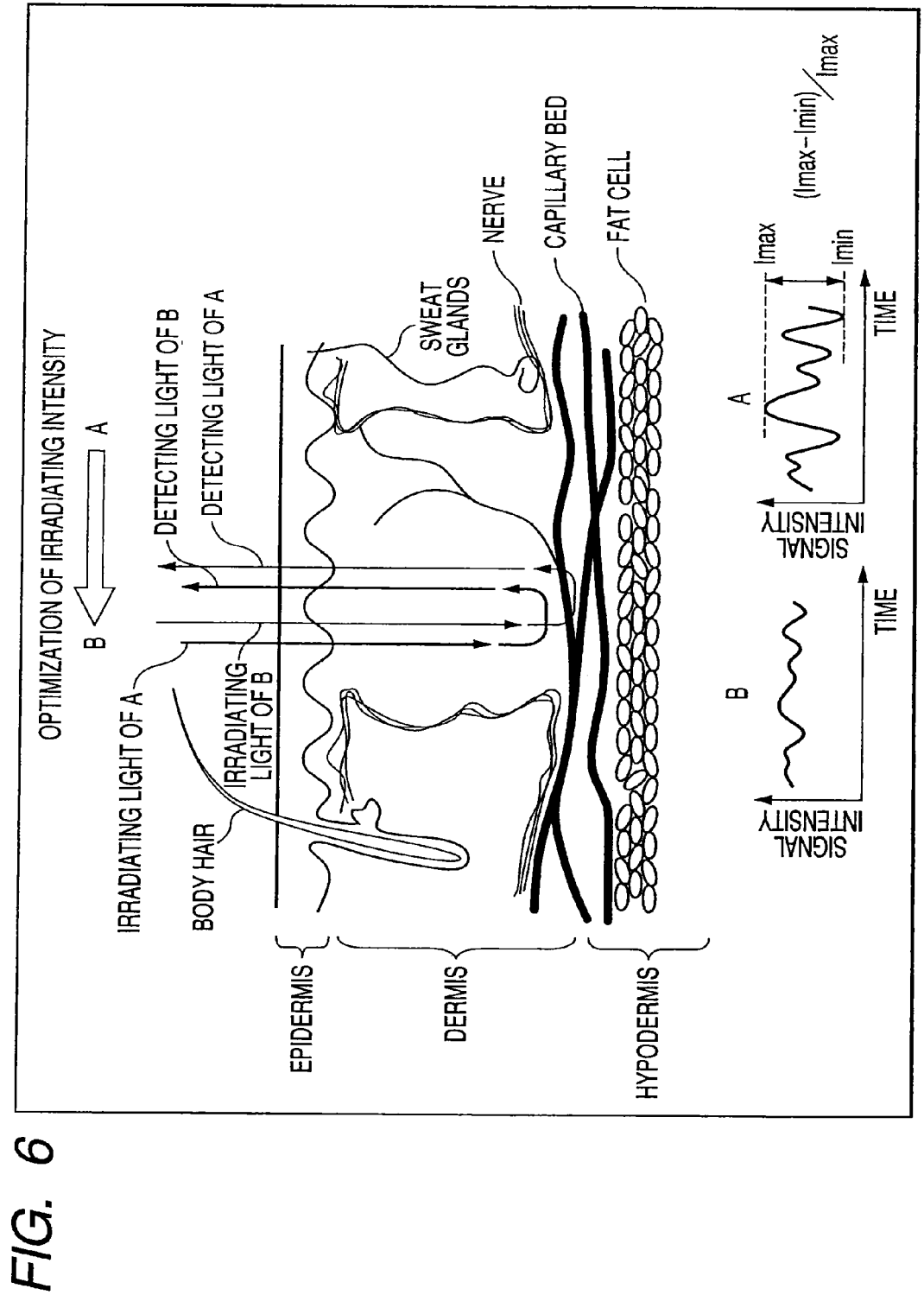
FIG. 6 is a schematic view of a preparatory measurement and irradiation intensity determination according to the second embodiment of the invention.

FIG. 6 schematically shows an example of a mechanism of a change in a signal by a difference in an irradiating intensity according to the embodiment. In irradiating light of A in FIG. 6, light transmitted through a portion of the blood vessel and therefore, a detecting signal of detecting light of A to be detected is varied, and a width of varying the signal is deviated from a predetermined proper range. On the other hand, in irradiating light at position B an irradiating intensity of which is made to be lower than that at position A, a depth of irradiating light invading the skin is reduced, and a variation in an optical signal by a portion of the blood vessel is restrained. Therefore, the width of varying the detecting signal of detecting light of B to be detected falls in the predetermined proper range, and a stable signal can be detected.

That is, by changing the irradiating intensity by changing the current applied to the light source portion 2-1 shown in FIG. 5, a depth of the irradiating light invading the skin is changed, for example, when the blood vessel causing the variation in the signal is present at a portion of an optical path of the deep portion of the organism, a variation in the optical signal can be restrained by reducing the irradiation intensity.

Figure 7:
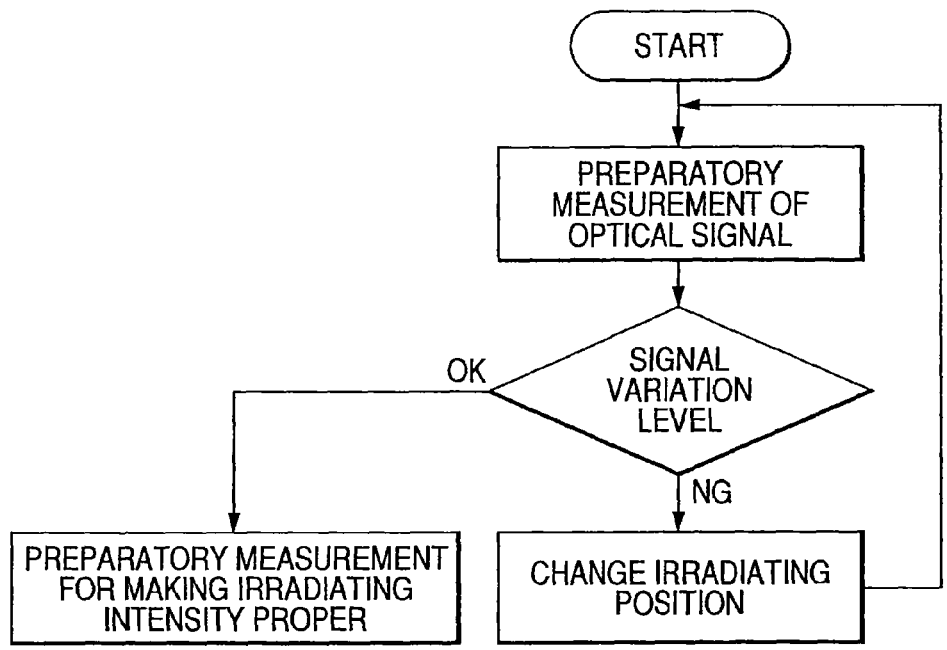
FIG. 7 is a diagram showing a procedure of a measurement processing according to the second embodiment of the invention.
Figure 8:
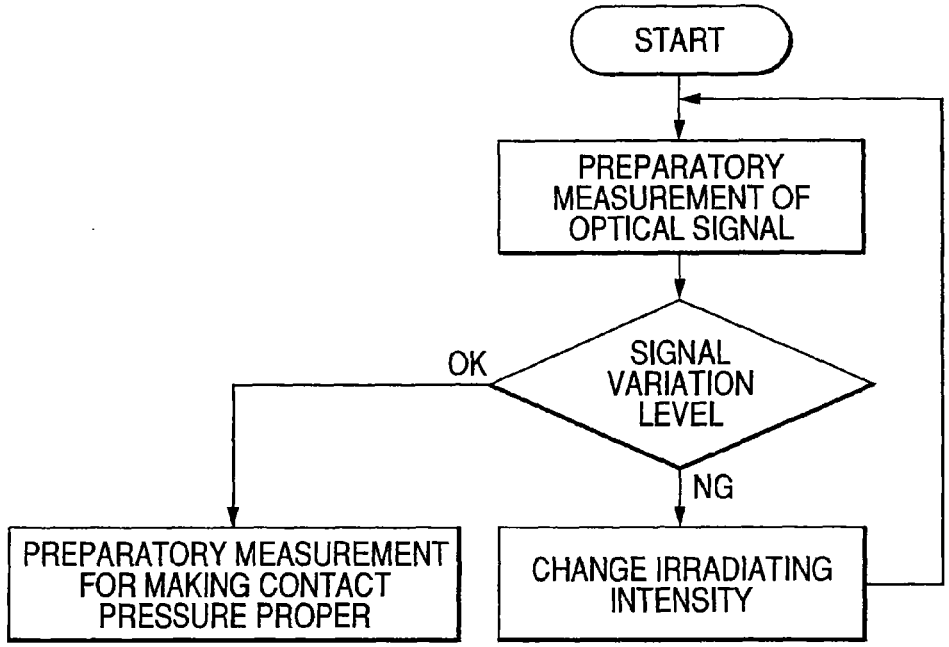
FIG. 8 is a diagram showing a procedure of a measurement processing according to the second embodiment of the invention.

FIG. 7 and FIG. 8 show a procedure of measurement processing for carrying out preparatory measurement for making the irradiating intensity proper and preparatory measurement for making a contact pressure proper based on a result of preparatory measurement of the optical signal shown in the first embodiment. The control portion 5 changes an irradiating position by controlling the moving mechanism drive portion 14 until the width of varying one set of light detecting signals becomes lower than the predetermined threshold, that is, the measuring position is determined to be proper in the position determining portion 3-4.

When the measuring position is determined to be proper, successively, operation of making the light irradiating intensity proper at the position is started. Preparatory measurement for making the light irradiating intensity proper at the position made to be proper is repeated.

As shown by FIG. 8, the irradiation intensity determining portion 3-6 determines that irradiation intensity is proper when a signal varying width of one set of light detecting signals falls in a range of, for example, ±1% which is a determination reference stricter than a determination reference for making the measuring position proper, and determines that the irradiation intensity is improper when the signal varying width does not fall in the range. The control portion 5 controls the light source portion 2-1 in order to change the irradiation intensity little by little until determining that the irradiation intensity is proper.

When the irradiation intensity is determined to be proper, successively, operation for making the contact pressure of the interface portion 8 to the body surface of the subject proper is started. Preparatory measurement for making the contact pressure proper is repeated by the position made to be proper and the irradiation intensity made to be proper.

Figure 10:
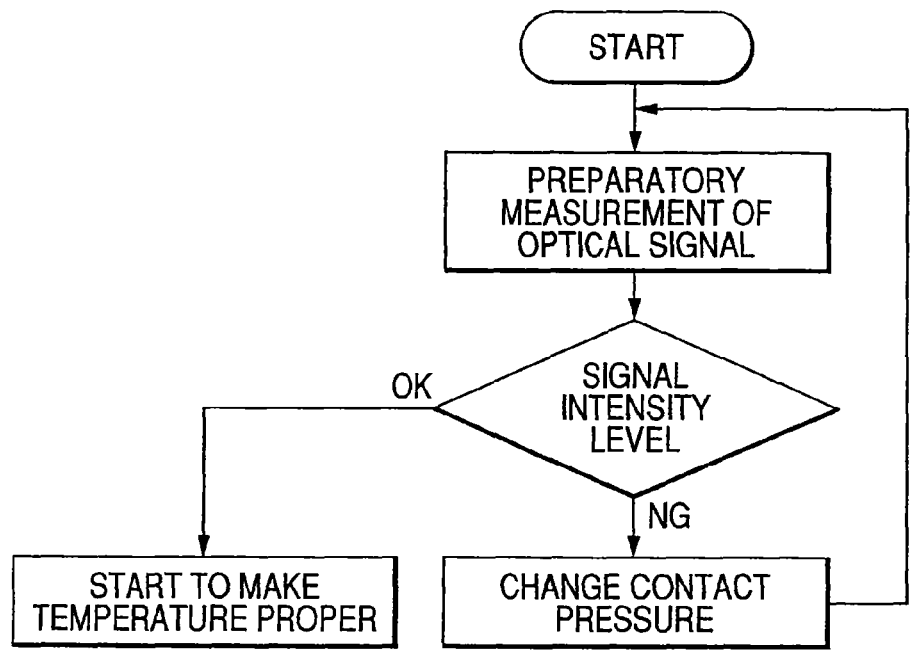
FIG. 10 is a diagram showing a procedure of a measurement processing according to the second embodiment of the invention.

As shown by FIG. 10, the contact pressure determining portion 3-7 determines that the contact pressure is improper when a signal intensity of at least one signal of one set of the light detecting signals becomes higher than a threshold for determining the contact pressure and determines that the contact pressure is proper when the signal intensity of all of signals of one set of the light detecting signals becomes lower than the threshold for determining the contact pressure. The control portion 5 changes the contact pressure between the subject 9 and the interface portion 8 by using the optical system up and down movable portion 13 until the contact pressure is determined to be proper.

A condition of bringing the subject 9 and the interface portion 8 into contact with each other is one factor of changing a dynamic state of the blood flow of the skin tissue portion, further, also a factor of changing a depth of invasion of the irradiating light to the skin or the intensity of the detecting signal of detecting light, by the embodiment, an optimum contact pressure condition is set in accordance with a measured portion for each subject and the contact pressure is controlled based on the condition.

For example, when a measured portion of the subject 9 is disposed at the forearm, the contact pressure between the forearm and the interface portion 8 can be determined to be 100 gf/cm$^2$.

When the measuring position, the irradiating intensity, the contact pressure are determined to be proper, successively, operation of making the body surface temperature of the subject proper is started.

Figure 9:
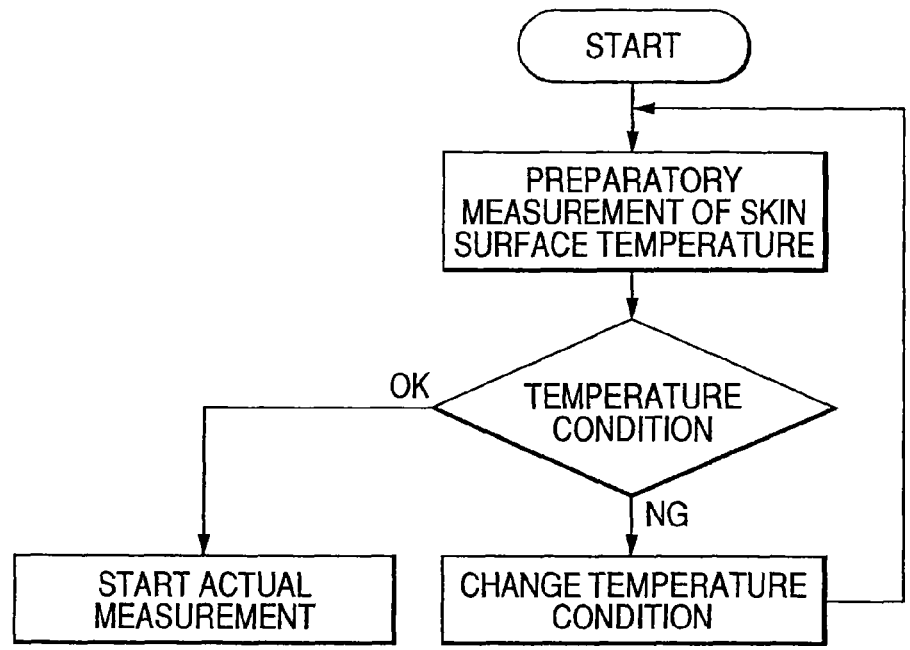
FIG. 9 is a diagram showing a procedure of a measurement processing according to the second embodiment of the invention.

FIG. 9 shows a procedure of controlling a temperature of a measured portion of the subject 9. In the procedure of the measuring processing of FIG. 9, the temperature control portion 10 for controlling a temperature of a measured portion arranged in the vicinity of the measuring portion of the subject 9 supplies a current to the Peltier element 15 until the body surface temperature of the measured portion by the temperature sensor 11 substantially coincides with the temperature suitable for measurement. There is carried out actual measurement for acquiring information with regard to a composition or a concentration of a desired substance present in the subject 9, or denaturing of the subject tissue under the condition.

Both of the measured portion of the subject 9 and the interface portion 8 depend on an environmental temperature, also temperatures thereof differ from each other and therefore, when the subject 9 is brought into contact with the interface portion 8, a physiological variation is applied to the subject 9 to constitute one factor of changing the intensity of the detecting signal of detecting light. The optimum temperature condition can be determined by the embodiment.

When the measuring position, the irradiating intensity, the contact pressure and the body surface temperature are made to be proper as described above, the actual measurement is started.

Although the description has been given of a constitution of carrying out the actual measurement after carrying out the preparatory measurement processing in the above-described various explanation, so far as the optimum measuring condition is acquired in the preparatory measuring processing, the actual measurement may naturally be constituted by the preparatory measurement.

According to the invention, there can be provided the living body information measuring apparatus capable of accurately carrying out a quantitative analysis or a qualitative analysis of the tissue condition of the subject by swiftly and accurately measuring the composition, the concentration of the body fluid or the tissue of the subject, or optical information related to a change in the physical property by preventing a failure of the measurement owing to the fact that the measured portion or the measuring condition is improper.

The invention claimed is:

1. A living body information measuring apparatus, comprising:
    means for irradiating light to a subject;
    means for detecting light from the subject;
    means for acquiring information with regard to a tissue condition of the subject based on a detecting signal of the light; and
    position determining means for determining an acceptability of a position of irradiating the light based on the detecting signal of the light,
    wherein the position determining means determines that the irradiating position is acceptable when a width of variation of the detecting signal of the light is lower than a threshold.

2. The living body information measuring apparatus according to claim 1, further including means for indicating the acceptability of the determined irradiating position by a lighted color of a display lamp or a message display of a display.

3. The living body information measuring apparatus according to claim 1, further including means for indicating the acceptability of the determined irradiating position by voice or a vibration.

4. The living body information measuring apparatus according to claim 1, wherein the information with regard to the tissue condition of the subject is a body fluid component concentration in a cell of an organism tissue, or outside the cell of the organism tissue, the body fluid component concentration is a glucose concentration, and in determining the glucose concentration, light having a wavelength selected at least from a region of 400 through 2500 nm is used.

5. The living body information measuring apparatus according to claim 1, wherein the information with regard to the tissue condition of the subject is a body fluid component concentration in a cell of an organism tissue, or outside the cell of the organism tissue, and
    wherein the body fluid component concentration is a concentration of hemoglobin included in the blood, and in determining the hemoglobin concentration, light having a wavelength selected from at least a region of 500 through 2500 nm is used.

6. A living body information measuring apparatus including:
    a light irradiating portion for irradiating light to a subject;
    means for detecting light diffused, transmitted or reflected in the subject;
    means for acquiring information with regard to a tissue condition of the subject based on a detecting signal of the light;
    position determining means for determining an acceptability of a position of irradiating the light based on the detecting signal of the light;
    a moving mechanism for moving the light irradiating portion substantially in parallel with a body surface of the subject; and
    control means for controlling the moving mechanism for moving the light irradiating portion when the position of irradiating the light is determined to be improper,
    wherein the position determining means determines that the irradiating position is acceptable when a width of variation of the detecting signal of the light is lower than a threshold.

* * * * *